United States Patent
Phillips et al.

(10) Patent No.: US 8,058,067 B2
(45) Date of Patent: Nov. 15, 2011

(54) SELF-ALIGNING TISSUE GROWTH GUIDE

(75) Inventors: James Phillips, London (GB); Robert Brown, Middlesex (GB)

(73) Assignee: The Open University, Buckinghamshire (GB)

( * ) Notice: Subject to any disclaimer, the term of this patent is extended or adjusted under 35 U.S.C. 154(b) by 1455 days.

(21) Appl. No.: 10/551,698

(22) PCT Filed: Apr. 2, 2004

(86) PCT No.: PCT/GB2004/001455
§ 371 (c)(1), (2), (4) Date: Aug. 21, 2006

(87) PCT Pub. No.: WO2004/087231
PCT Pub. Date: Oct. 14, 2004

(65) Prior Publication Data
US 2007/0168044 A1    Jul. 19, 2007

(30) Foreign Application Priority Data
Apr. 3, 2003 (GB) .................................. 0307751.8

(51) Int. Cl.
C12N 11/00 (2006.01)
A61F 2/00 (2006.01)
A61F 2/04 (2006.01)

(52) U.S. Cl. ........ 435/402; 435/174; 435/382; 606/152; 623/11.11; 623/23.76

(58) Field of Classification Search .................. 606/152; 623/11.11, 23, 76
See application file for complete search history.

(56) References Cited

U.S. PATENT DOCUMENTS

| 5,756,350 | A | 5/1998 | Lee et al. |
| 5,948,654 | A * | 9/1999 | Tranquillo et al. ........... 435/174 |
| 6,171,610 | B1 | 1/2001 | Vacanti et al. |
| 6,174,333 | B1 | 1/2001 | Kadiyala et al. |
| 6,461,629 | B1 * | 10/2002 | Tranquillo et al. ........... 424/422 |

FOREIGN PATENT DOCUMENTS
WO     02/47557 A1    6/2002

OTHER PUBLICATIONS

Nyberg et al. 1993. Evaluation of a Hepatocyte-Entrapment Hollow Fiber Bioreactor: A Potential Bioartificial Liver. Biotechnology and Bioengineering, vol. 41, pp. 194-203.*
International Search Report of PCT/GB2004/001455, mailed May 26, 1998.
Chen et al., "Peripheral nerve regeneration using silicone rubber chambers filled with collagen, laminin and fibronectin", Biomaterials, vol. 21, No. 15, Aug. 2000, pp. 1541-1547, XP004204628.
Hentz et al., "The nerve gap dilemma: A comparison of nerves repaired end to end under tension with nerve grafts in a primate model", The Journal of Hand Surgery, May 1993, pp. 417-425, XP009033626.

* cited by examiner

*Primary Examiner* — Ralph Gitomer
*Assistant Examiner* — Kailash Srivastava
(74) *Attorney, Agent, or Firm* — Nixon & Vanderhye P.C.

(57) ABSTRACT

The present invention relates to artificial tissue growth guides comprising a core and an outer sleeve, which facilitates the regeneration of damaged tissues, such as nerves. The core is fixed to the sleeve at two attachment sites so that cells seeded within the core produce mechanical tension between the attachment sites. This tension aligns the cells and the fibres of the core and provides an improved substrate for tissue regeneration. Growth guides may be surgically implanted into an individual.

28 Claims, 3 Drawing Sheets

SELF-ALIGNING TISSUE GROWTH GUIDE

This application is the US national phase of international application PCT/GB2004/001455, filed 2 Apr. 2004, which designated the U.S. and claims priority of GB 0307751.8, filed 3 Apr. 2003, the entire contents of each of which are hereby incorporated by reference.

This invention relates to artificial guides which facilitate the growth of tissues, such as nerves, and may, for example, be surgically implanted into an individual to facilitate the regeneration of damaged tissue.

Damaged tissue within the body is usually repaired by natural processes of regeneration. However, in certain circumstances, the regeneration of damaged tissue is either limited or does not occur at all. Damage to nerves in the peripheral (PNS) or central nervous system (CNS), for example, following trauma or surgery, often results in the permanent loss of sensitivity or function.

Artificial guides have been developed to facilitate the regeneration of neural tissue in both the CNS and PNS. Tubes made from collagen (Labrador et al (1998) Exp. Neurol. 149 243-252) hyaluronan or polylactone have been used to provide global guidance to the neurite outgrowth and isolate the repair region by virtue of the tubular structure. Alternatively, bundles of aligned fibres made from carbon filaments (Khan et al (1991) Brain Res 541 139-145), nitrocellulose paper (Houle et al (1989) Neurosci Lett 103, 17-23), collagen (Liu et al (1997) Neurosci Res 49 425-432; Yoshii and Oka, (2001) J. Biomed. Materials Res. 56 400-405) or fibronectin (Priestley et al (2002) J. Physiol-Paris 96 123-133) have also been used to provide contact guidance at a cellular level (reviewed by Brown, (2000) Bioartificial Implants: Design and Tissue Engineering in Structural Biological Materials, design and structure property relationships (Ed M. Elices) Pergamon Materials Series Vol. 4 151-160).

Artificial guides may, for example, be implanted into a site of nerve damage such that the ends of the guide contact the proximal and distal stumps of the damaged nerve. The regenerating nerve grows from the proximal stump into the proximal end of the guide and then through the guide to contact the distal nerve stump at the distal end of the guide and eventually to re-establish a neural connection.

Artificial materials may be used in a nerve guide either alone or with the addition of growth factors (Whitworth et al (1995) Eur. J. Neurosci. 7:2220-2225). Seeding of implants with neural repair cells, which produce growth factors, e.g. Schwann cells, is known to facilitate nerve regeneration (Rodriguez et al (2000) Exp. Neurol. 161 571-584).

Although artificial implants have produced some encouraging results, no functional regeneration of nerves of either the central (CNS) nervous system has yet been achieved following trauma or injury.

The present inventors have produced a guide for tissue growth which is seeded with cells. The guide is arranged such that a uni-axial mechanical tension is generated internally within the guide. This tension auto-aligns the cells in the direction of tissue growth to provide a cellular guidance substrate for the regenerating tissue in vivo.

One aspect of the invention provides a tissue growth guide for tissue growth comprising,
an inner core comprising a biopolymer matrix having one or more tension generating cells disposed therein,
the guide further comprising an outer sheath surrounding said inner core,
said inner core being fixed to said outer sheath at a first attachment region and a second attachment region; such that, in use, the cells in said matrix generate mechanical tension in the core between the first and second attachment regions.

Initially, when the core is fixed to the sheath at the first and second attachment regions, there is no tension in the core. When the core is in place within the sheath, cells within the core begin to produce a contractile force. The contractile force generates a tensional load within the matrix between the first and second attachment regions. This mechanical tension load is largely co-axial and runs parallel to the direction of tissue re-growth (i.e. longitudinally through the core). The first attachment region is preferably at or adjacent the proximal (entry) end of the guide and the second attachment region is preferably at or adjacent the distal (exit) end of the guide, although in some embodiments the outer sheath may extend beyond the core at each end, for example to facilitate contact with the tissue stumps flanking the damaged region.

The presence of mechanical tension within the surrounding matrix causes the cells within the matrix to align co-axially along the core, i.e. in the direction of re-growth. The tension in the core may also cause the fibres of the matrix to move into a comparable alignment.

Cell level guidance via alignment of extracellular matrices optimises cell migration and is advantageous in a tissue repair guide (Ahmed & Brown (1999) Cell. Motil. Cytoskeleton 42 331-343; Priestley et al (2002) J. Physiol. Paris 96 123-133; Wojciak-Stothard et al In Vitro Cell Dev. Biol. Anim. 33 110-117).

Tissues suitable for repair as described herein may regenerate or re-grow in a uni-directional manner from one damaged tissue end to the other (e.g. a nerve) or in a bi-directional manner from both damaged tissue ends (e.g. non-neural tissue such as tendon, ligament, meniscus, blood vessel, skin, digestive tract and bone).

Suitable tissues include muscles (in particular neuro-muscular junctions), blood vessels, tendons, ligaments, capsules, meniscus, bones skin and nerves. Some preferred embodiments are directed to the repair of nerves and neural tissue.

The inner core of the guide is preferably linear i.e. it is significantly larger in one dimension than in the other two, and is conveniently rod shaped i.e. it has a round, for example circular or elliptical, cross-section. In embodiments in which the guide is adapted for implantation, the inner core may have a size (i.e. diameter) and length appropriate to connect different tissues and anatomical regions. For example, an inner core suitable for connecting the digital nerve may be about 1 mm diameter. Other cores suitable for repair of human nerves may be from 2-7 mm diameter.

The biopolymer matrix of the inner core may be a protein-based fibrillar substrate, preferably self-gelling, which is compliant and contractable by the forces generated by embedded cells. Suitable materials include collagen, fibrin/fibrinogen, fibronectin, gelatin, and biosorbable polymers such as polylactide, polyglycolic acid, and polycapryolactone. Preferably, the biopolymer matrix does not naturally occur in the mammalian body and does not exhibit the organisation and gross morphology of mammalian tissue.

A suitable collagen matrix may be a gel formed of reconstituted network of entangled collagen fibrils of 20-500 nm diameter, typically comprising 90%-99% interstitial liquid, depending on the collagen source and reconstitution method.

Suitable collagen matrices include collagen type I matrices which may conveniently be prepared as described in Mudera V.C. et al Cell. Motil. Cytoskeleton (2000) 45 1-9.

A cell suitable for use in the invention applies a contractile force to the biopolymer matrix and falls into alignment with the resultant tension in the matrix. Preferred cells also facilitate growth of tissue within the matrix, for example, by producing one or more appropriate growth promoting factors. For example, a cell suitable for use in the growth of neural tissue (i.e. a neural repair cell) may produce one or more neural growth promoting factors. Neural growth promoting factors include neurotrophins such as neurotrophin-3, nerve growth factor (NGF), glial growth factor (GGF) and brain derived neurotrophic factor (BDNF). Preferably, the cells seeded within the biopolymer matrix align and contract but do not proliferate to form organised tissue.

Suitable cells for use in seeding the matrix include mammalian cells such as Schwann cells, neural fibroblasts, fibroblasts, tenocytes (osteoblasts), myoblasts, smooth muscle cells and endothelial cells. Cells suitable for neural repair include Schwann cells, neural fibroblasts and mixtures thereof (Hall S (2001) J. Hand Surg. 2613 (2) 129-136). Neural repair cells may be obtained from adult nerves by collagenase digestion or explant culture, as described in 'Neural Cell Culture, a practical approach' Ed Cohen & Wilkin 221-236 IRL Press.

Preferably, the cells do not produce polypeptides of a type or amount which is not normally found in the tissue of interest (e.g. nerve tissue). For example, in preferred embodiments, the cells do not contain foreign DNA for expression of a heterologous protein.

In some embodiments, in addition to tension generating cells (e.g. fibroblasts), the matrix may also be seeded with cells from the tissue of interest. For example, tenocytes, endothelial or epithelial cells, secretory or gland vessels (e.g. sebaceous, pancreatic islet cells, adrenal cortex cells), melanocytes, Schwann cells or astrocytes may be used. In such embodiments, the core containing the aligned tension-generating cells forms a guidance substrate for the growth of the embedded tissue cells.

In other embodiments, the matrix is not seeded with cells from the tissue of interest. In other words, cells within the guide are heterologous to the tissue of interest. For example, the matrix may be devoid of neurons prior to implantation.

Cells may be seeded within the matrix by mixing them with the liquid biopolymer matrix and then allowing the liquid matrix to solidify into a gel. Conveniently, the gel may be seeded with 104 to $10^7$ cells per ml, more preferably $2 \times 10^5$ to $10^6$ cells per ml.

The outer sheath is preferably a solid material that provides resistance to the contractile force imparted by the cells in the core, thereby maintaining mechanical tension within the core between the two attachment regions. The outer sheath material is therefore stiff relative to the core biopolymer matrix, in order to accommodate mechanical tension in the core. The sheath material preferably shows low adhesion or substantially no adhesion with the core outside the attachment regions. Preferably, the sheath fully surrounds the core, such that only the ends of the core are exposed to the exterior.

Suitable sheath materials have high biocompatibility i.e. do not produce adverse reactions within the body, and, in preferred embodiments, are resorbable in situ, for example biodegradable, in order to avoid the need for surgical removal from the application site after use. Examples of suitable sheath materials include phosphate glass, polylactone, polyglycone, polycapryolactone and hyaluronan or derivatives thereof. Other suitable materials include collagen, fibrin, fibronectin, cellulose, chitosan, and starch. Suitable non-resorbable sheath materials include silicone.

In some embodiments, the sheath is non-porous.

If the core is a non-protein polymer, the proximal end of the sheath may comprise a protein aggregate material to allow the core to be preferentially released from the proximal end, mediated by cell proteases from the incoming tissue (e.g. a regenerating nerve).

The outer sheath is fixed to the inner core at the first attachment region and the second attachment region such that movement, particularly axial or longitudinal movement, of the core relative to the sheath is prevented in these regions. To allow the generation of a contractile force, the core is preferably free to move relative to the sheath between the first and second attachment regions. To prevent adhesion of the core to the sheath outside the defined attachment regions, the sheath material is preferably non-adherent.

The core and sheath may be fixed together in the attachment regions by any convenient method and the skilled person is able to identify a number of suitable techniques.

In some embodiments, the outer sheath may be mechanically fixed to the core, i.e. the biopolymer matrix, at the first and second attachment regions.

For example, at the first and second attachment regions, the outer sheath may be shaped to provide a cooperative engagement with the inner core. The engagement fixes the sheath and core together at these regions. Preferably, the outer sheath comprises one or more openings or protrusions in its inner surface. openings may extend through the side of the sheath to the outer surface, or may form recesses or niches that do not extend to the outer surface. Suitable openings include slots, pores, grooves, and apertures. For example, the attachment regions of the sheath may comprise porous cuffs around the core.

Preferably, the core engages with the openings or protrusions in the sheath when it is introduced into the sheath in liquid form during production of the guide. When the core solidifies, the engagement holds the core and sheath together at the attachment regions.

Other mechanical fixing methods, such as pins, sutures, pressure clips or insert clamps, may also be used.

In some embodiments, the outer sheath may be chemically fixed to the core at the first and second attachment regions, for example using an adhesive such as a fibrin or cyanoacrylate adhesive.

As described above, in some embodiments, the guide may be adapted for implantation into an individual to facilitate the repair of damaged tissue.

The outer sheath may, for example, be composed of a non-adherent material which reduces or abrogates the formation of adhesions between the guide and the tissue surrounding the implanted guide (i.e. the sheath is anti- or non-adhesive to surrounding gliding tissue layers). The outer sheath may also reduce or abolish the in-growth of surrounding cells or tissues into the inner core.

The sheath may also be suitable and/or adapted for accepting sutures or other attachment means (e.g. glue) to hold the core against the damaged tissue ends.

A guide adapted for implantation is preferably resorbable in situ. More preferably, the stability of the guide (and therefore the resorption rate) varies along its length (e.g. where tissue regenerates in a proximal to distal direction, there may be a gradation in the rate of resorption of the guide between the proximal (entry) and distal (exit) ends and where tissue regenerates from both broken tissue ends (i.e. both ends are proximal), there may be a gradation in the rate of resorption of the guide between the ends of the guide and the middle).

Where tissue regenerates in a proximal to distal direction, for example in nerve repair, the gradation of resorption rate is preferably such that the proximal end of the guide is resorbed more quickly than the distal end. This provides the regenerating nerve end with extended guidance as it passes through the guide. The secretion of cellular factors, including proteases, by the regenerating nerve causes preferential proximal resorption as the nerve enters and grows through the proximal end of the guide.

The resorption of the outer sheath at the first attachment region, after regenerating tissue, such as a nerve, has entered the proximal end of the core, releases the core from the outer sheath at the proximal end. The core is held at its proximal end by the tissue itself and tension previously exerted between the first and second attachment regions is transferred to the regenerating tissue, exerting a traction force. In other words, the outer sheath at the first attachment region is resorbed preferentially after entry of regenerating tissue into proximal end of the core, such that the core applies mechanical tension to the regenerating tissue.

Where tissue regenerates in a multidirectional manner (i.e. from both broken ends of the damaged tissue), the gradation of resorption rate is preferably such that the ends of the guide (which are both effectively proximal ends) are resorbed more quickly than the middle of the guide. This provides the regenerating tissue ends with extended guidance as they pass through the guide and meet within it. This preferential resorption is caused by the release of cellular factors, including proteases, by the regenerating tissue as it enters and grows through the guide.

The resorption of the outer sheath at the first and second attachment regions, after regenerating tissue has entered the ends of the core, releases the core from the outer sheath. The core is held at its ends by the regenerating tissue itself and tension previously exerted between the first and second attachment regions is transferred to the plane of the prospective tissue growth, exerting a traction force. In other words, the outer sheath at the first and second attachment regions is resorbed preferentially after entry of regenerating tissue into the ends of the core, such that the core applies mechanical tension to the regenerating tissue.

This is advantageous, as the application of mechanical tension to tissue, in particular to nerves, is known to accelerate growth (Smith et al (2001) Tiss Eng. 7 131-139).

Whilst preferential proximal resorption may occur automatically, as the regenerating tissue enters the guide, resorption rate may be further controlled across a guide having a protein-based sheath by soaking one or both ends of the guide in stabilizing reagents such as $Cu^{++}$ or $Zn^{++}$ solutions, to generate a concentration gradient of these ions across the guide, or by fabricating the guide from a number of lengths of guidance material whose adhesion protein composition gradually changes from the proximal to the distal end of the guide.

In use, a guide of the invention may be assembled and optionally, tension in the core allowed to develop prior to implantation, for example by culturing the cells within the core for 8-12 hours. The guide may then be implanted into a site of tissue damage such that the ends of the inner core contact the proximal and distal stumps of the damaged tissue. The guide may be held in place by glue or other fixing means, such as sutures, for example through the outer sheath. In some embodiments, the fixing means may be comprised within the guide. The proximal stump of the regenerating tissue, such as a nerve, may enter the guide at its proximal end and exit the guide at its distal end to contact the distal stump. In other embodiments, regenerating tissue from both broken stumps may enter the guide at its ends and meet within the guide to re-establish a functional connection.

Guides as described herein may be useful in the repair of damage to a variety of tissues, including neural damage in the central or peripheral nervous system, and generation of grafts for plastic surgery.

A tissue growth guide as described herein may be linear and have a first and a second end. In embodiments in which tissue regrowth is unidirectional, the first end may act as a proximal entry port for the regenerating tissue and the second end as a distal exit port. In embodiments in which tissue regrowth is bi-directional, the first and second ends may both act as proximal entry ports for the regenerating tissue.

In some embodiments, the guide may be branched i.e. it may comprise more than two ends, for example, third or fourth ends. Such a branched guide may possess more than one entry port and/or more than one exit port. Preferred embodiments may comprise a single proximal entry port and two or more, for example three, four or five, distal exit ports. A guide according to these embodiments preferably comprises an attachment region at each of its ends to allow mechanical tension to be maintained throughout the core. For example, a first attachment region may be positioned adjacent the proximal entry port and a second and third (or more) attachment regions respectively at the two (or more) distal exit ports.

In other embodiments, a guide of the invention may be adapted for the in vitro growth of tissue. Tissue grown within such a guide may, for example, be subsequently implanted into an individual.

In such embodiments, the cells seeded in the biopolymer matrix may comprise tension generating cells, such as fibroblasts, and additionally cells of the tissue of interest (or progenitor/stem cells capable of differentiating into cells of the target tissue). Suitable tissue cells include tenocytes, endothelial or epithelial cells, secretory or gland vessels (e.g. sebaceous, pancreatic islet cells, adrenal cortex cells), melanocytes, Schwann cells or astrocytes.

A guide seeded with tension generating cells and cells of the target tissue may be cultured in a bioreactor under standard tissue culture conditions (for example, 37° C. in DMEM+10% Foetal Calf Serum) to allow the orientated growth of target tissue cells within the guide.

The guide may be cultured by immersion in culture medium and/or medium may be introduced directly to the interior of the guide by means of capillaries within the core.

The core of a guide according to these embodiments may comprise one or more capillaries for the passage of nutrient medium through the core. Preferably, the one or more capillaries form continuous channels running co-axially along the length of the core.

Capillaries may be introduced to the core during production by conventional techniques such as incorporation and removal of fine suture wire, incorporation of a soluble fibre, introduction of a chemically degradable layer, or treatment with an optical/radiation source such as a laser.

The one or more capillaries may be connected to a source of nutrient medium. Flow of medium through the capillaries may be induced, preferably by pumping, for example using a peristaltic pump. Flow through the capillaries may be linear, pulsed or cyclical. Medium flowing through the capillaries diffuses through the core to provide suitable growth conditions to the embedded cells.

Two or more tissue growth guides in accordance with this embodiment may be incubated in a common flow controlled bioreactor by connecting an end of the guide to a flow manifold, for example using a luer-syringe type connection, such that nutrient medium flows from the manifold through the capillaries of the core and then on to an outflow.

After growth within the guide, tissue cells may be isolated and or extracted from the guide and used for a variety of purposes, including implantation at a site of tissue damage.

A tissue growth guide as described herein may be produced by introducing the inner core to the outer sheath in a liquid form, so that the sheath moulds the core to the appropriate shape.

An aspect of the invention provides a method of making a guide for tissue growth comprising;
providing an outer sheath,
introducing cells to a liquid biopolymer matrix,
introducing said liquid matrix to the interior of the outer sheath,
causing or allowing said liquid matrix to set; and,
fixing the matrix to the sheath at first and second attachment regions.

The matrix may be fixed to the sheath by any one of a range of mechanical or chemical techniques as described above.

Preferably, the sheath and the matrix are fixed together at the attachment regions through the cooperative engagement of the matrix with the sheath.

A method of making a guide for tissue growth may comprise;
providing an outer sheath which is shaped to cooperatively engage the inner core at the first and second attachment regions,
introducing cells to a liquid biopolymer matrix,
introducing said liquid matrix to the interior of the outer sheath such that liquid matrix engages said sheath at the said attachment regions, and;
causing or allowing said liquid matrix to set, such that said engagement prevents co-axial movement of the core relative to the sheath.

The outer sheath may be linear or may have one or more branches e.g. it may be bi- or tri-furcated. The core, which is moulded by the sheath, will naturally adopt the shape of the sheath.

The matrix may be set or solidified by any convenient technique to form the core of the guide, for example incubation at 37° C. for 5 minutes; addition or activation of thrombin in a fibrinogen containing protein solution (e.g. by adding $Ca^{2+}$ to a plasma fraction); shear aggregation of fibronectin rich protein gels (Brown et al (1994) Biomaterials 15 457-464; Phillips et al (2003) in press), or addition of polymerising catalyst to self-setting biodegradable polymers.

Suitable biopolymer matrices, cells and outer sheaths are described above.

In other embodiments, the seeded biopolymer matrix may be introduced to the outer sheath in a non-liquid i.e. gel form and then fixed at the first and second attachment regions. For example, the matrix may be inserted into a tubular outer sheath or the sheath may be wrapped around or applied to the matrix (e.g. by casting a catalysed setting sheath material around the core (e.g. a fibrin rich material or self-setting biodegradable polymer)). The sheath may then be fixed in place. Suitable fixings prevent the axial movement of the core relative to the sheath and may include adhesives, pins, clamps and pressure clips.

A method of producing a tissue growth guide may comprise the further step of; causing or allowing the cells within said matrix to generate mechanical tension between the first and second attachment regions.

Mechanical tension may be generated in the core by culturing the cells in the matrix in appropriate conditions, for example, by placing the guide in a standard cell culture media, such as DMEM, for example in a petri dish, and incubated for 8 to 12 hours at 37° C. The cell culture medium may optionally be supplemented with ascorbate, to facilitate contraction.

Preferably, the cells in the guide of the invention do not proliferate to form an organised tissue within the matrix.

Culture conditions for generating mechanical tension are distinct from conditions for cellular proliferation to form organised tissue, which requires for example, incubation periods of 1 to 18 days. The presence of heterologous organised tissue within the guide may impede the progress of the regenerating endogenous tissue through the guide.

In some preferred embodiments, the guide may then be implanted into a human or animal body for the repair of damaged tissue. For example, the proximal end of the guide may be attached to the broken ends of a damaged tissue of the guide may be attached to the distal stump of a damaged nerve. Where the tissue is a nerve, the proximal end of the guide may be attached to the proximal stump of the damaged nerve and the distal end of the guide may be attached to the distal stump of the damaged nerve.

A tissue growth guide may optionally be implanted without a pre-tensioning step as described above. Mechanical tension is then generated in the core in situ.

In other preferred embodiments, the one or more tissue repair cells in the biopolymer matrix may comprise fibroblasts or other tension generating cells, as described above, and additionally cells of the tissue of interest (or progenitor/stem cells capable of differentiating into target tissue cells). Suitable tissue cells include tenocytes, endothelial or epithelial cells, secretory or gland vessels (e.g. sebaceous, pancreatic islet cells, adrenal cortex cells), melanocytes, Schwann cells and astrocytes.

A method according to such embodiments may comprise, after mechanical tension has been generated in the core by the tension generating cells, the step of culturing the tissue cells in said guide. Cells may be cultured by the addition of nutrient medium and appropriate conditions, as described above.

After culturing, the cells in said core may be isolated and or extracted from the guide, for example, for use in therapy, according to standard techniques. In other embodiments, the core or the guide containing the cultured tissue cells may be used directly in therapy, for example implantation for the repair of damaged tissue.

Other aspects of the invention provide a guide as described herein for use in a method of repairing tissue damage, in particular neural damage, and a method of repairing tissue damage to an individual comprising implanting a guide as described herein into said individual.

Implanting may comprise attaching or fixing the guide to the broken ends of a damaged tissue (e.g. the proximal and distal stumps of a damaged nerve), for example using sutures.

Another aspect of the invention provides a method of repairing tissue damage comprising attaching the proximal end and distal ends of a guide as described above to the broken ends of a damaged tissue in an individual (e.g. the proximal and distal stumps respectively of a damaged nerve).

Another aspect of the invention provides a kit comprising a guide for tissue growth as described above or for the production of a guide for tissue growth as described above. A kit may comprise a biopolymer matrix, for example in a solid or liquid form, an outer sheath and one or more tension generating cells and/or cells from a tissue of interest.

Suitable biopolymer matrices, outer sheaths and neural repair cells are discussed above.

The matrix may be a ready prepared gel pre-shaped into the appropriate core shape or may be in a powder or liquid form for moulding into the appropriate core shape using the outer sheath.

The outer sheath may be in the form of a tube which surrounds the inner core, or into which the inner core can be introduced.

Alternatively, the outer sheath may be in the form of a flat sheet that is wrapped around or applied to the core prior to the development of pre-stress in the core and implantation.

A kit may comprise one or more additional components such as suturing equipment or glue for fixing the guide to the damaged tissue ends, additional growth factors for incorporating into the inner core and instructions for use.

Aspects of the present invention will now be illustrated with reference to accompanying figures and the experimental exemplification below, by way of example and not limitation. Further aspects and embodiments will be apparent to those of ordinary skill in the art.

It will be understood by those of ordinary skill in the art that features described in this specification may be used in any combination in accordance with the invention.

All documents mentioned in this specification are hereby incorporated herein by reference.

EXPERIMENTAL

Figure 1:
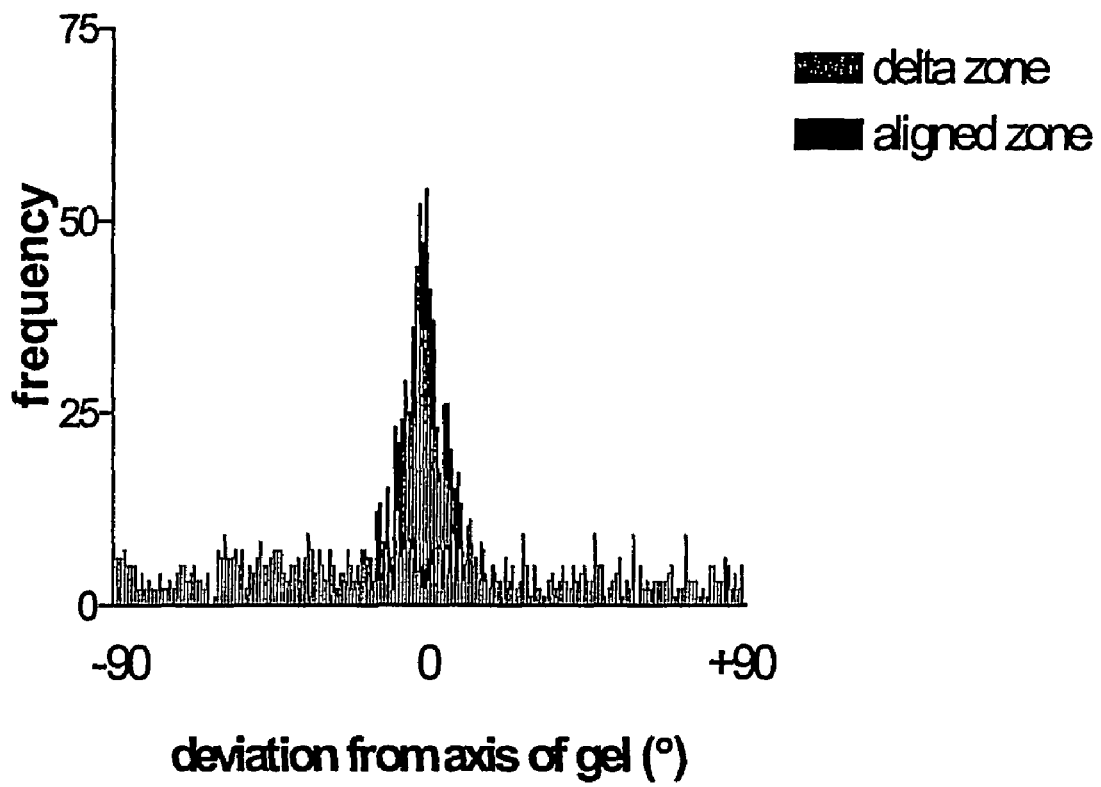
FIG. 1 shows data from fluorescent immunostaining experiments which indicate that DRG axons are orientated with the aligned Schwann cells within tethered collagen gels

Materials and Methods
Cell-Seeded Collagen Gels for In Vitro Testing

Collagen gels were created in a culture system in order to test the effectiveness of aligned Schwann cells on the growth of neurones. The method follows that developed previously by this group (Eastwood et al. (1994) Cell Motil Cytoskeleton. 1998; 40(1):13-21) but used primary cultures of Schwann cells.

Preparation of Schwann Cells

The method for primary rat Schwann cell cultures was adapted from Wigley and Hall (1998) Glia 24; 290-303. Briefly, four male Fisher rats (150-200 g, Harlan) were sacrificed by $CO_2$ asphyxiation. Using a dissecting microscope, each sciatic nerve was exposed in mid-thigh and all major branches of the common peroneal and tibial nerves dissected out. The nerves were then washed twice in Hnak's Balanced Salt solution (HBSS, Gibco) containing 50 µg/ml Gentamycin (Sigma). The epineurium and perineurium were then stripped off using fine forceps under the dissecting microscope. Individual nerves were chopped into 1×1 mm segments with a McIlwain tissue chopper and placed in 35 mm dishes containing Dulbecco's Modified Eagle's Medium (DMEM) (GIBCO, Grand Island, N.Y.), supplemented with 10% fetal calf serum (FCS), (DMEM/FCS), and 50 µg/ml gentamycin. Explants were left floating in this medium for 4 days at 37° C./10% $CO_2$. Eighteen hours before dissociation, collagenase/dispase (0.1%, Boehringer Mannheim Biochemicals, Indianapolis, Ind.) was added to the medium and the explants were dissociated on day 4 by gentle trituration through a flame-narrowed pipette (0.5-1 mm bore). Cells were then plated at $5×10^4$ cells/ml in DMEM/FCS supplemented with 20 mg/ml GGF-2 and 10 ng/ml Forskolin (Sigma) on to polylysine/laminin coated 25 $cm^2$ tissue culture flasks and returned to culture for a maximum of 5 days before use. Cells were harvested immediately prior to incorporation into the collagen gels. The cell monolayer was washed with $Ca^{2+}$ and $Mg^{2+}$ free PBS before 3 ml of 0.125% trypsin (in 0.01% w/v EDTA in PBS) was used to detach the cells from the flask surface. 3 ml of DMEM/FCS was then added to inactivate the trypsin. Cells were triturated through a flame-narrowed pipette (0.5-1 mm bore), harvested by centrifugation at 1500 rpm for 5 minutes and resuspended in the DMEM/FCS.

4 ml of 2 mg/ml of type I rat tail collagen was mixed with 0.5 ml 10×DMEM and neutralised with 1M NaOH prior to the addition of 0.5 ml Schwann cell suspension (mixture of Schwann cells and fibroblasts from primary culture of adult rat sciatic nerve explant prepared as described above; 250 000 cells per ml). This mixture was cast into two rectangular moulds (2.5 ml into each) and formed a gel within 5 min at 37° C. The rectangular gels were tethered at their ends with porous mesh that integrated with the ends of the gel and formed a tethering bar. Once the gels had set, the moulds were topped up with 7 ml of media (DMEM, 10% FCS, penicillin/streptomycin) supplemented with 50 µg/ml ascorbic acid and incubated for 18 h at 37° C. to allow contraction and alignment.

DRGs were harvested from a freshly culled adult SD rat (200 g) and cleaned of all nerve processes. DRGs were then incubated in DMEM containing 0.125% collagenase for 90 min at 37° C., then the collagenase solution was removed and a cell suspension was created by trituration of the DRGs in culture media. Debris were allowed to settle and the cell suspension was removed, centrifuged for 5 min at 100 g then the cells were resuspended in 0.5 ml culture media. A rectangular tethered collagen gel was seeded with Schwann Cells and allowed to contract for 18 h as described above.

Culture medium was drained from the aligned Schwann cell gels and 250 µl of the DRG suspension was added to the surface of the gel. The gel was left for neurones to adhere for 10 min before being topped up with 7 ml culture media (DMEM+10% foetal calf serum) and incubated for 3 days at 37° C. in a humidified atmosphere with 5% CO2.

Immunostaining of Collagen Gels

After 3 days incubation, media was removed and gels were washed briefly with PBS prior to fixation for 20 min in 4% paraformaldehyde in phosphate buffer. Gels were stained for the presence of β-tubulin, which is a marker for neurones. All reagents were made in PBS and all incubations and washers were at room temperature. Briefly, gels were incubated in 0.1% Triton-X for 10 min, then blocked using 5% swine serum prior to incubation in mouse anti-β-tubulin (1:400) (Sigma) for 1 h. The secondary antibody was antimouse IgG (1:100) conjugated to TRITC, for 45 min. Between incubations, gels were washed for 3×15 min in 5 ml PBS, and prior to visualization, gels were stored for at least 24 h in 5 ml PBS at 4° C.

Neuronal growth was visualised using a fluorescent microscope (Nikon Diaphot) linked to a digital video camera (Hammamatsu Orca). Images were captured from fields representative of the central region of the gel (containing the aligned contracted Schwann cells) and the stress-shielded delta zones at each end. Approximately 40 images were captured from each zone of 2 gels and the angle of each axon path was calculated using Openlab software (Improvision, UK) on a Macintosh G4. The angle of deviation from the longitudinal axis of the gel was calculated and the frequency (number of axons) with each angle is shown. For the aligned zones, a total of 744 axons were traced and for the delta zones, 766 were traced.

Construction of Implantable Tissue Guides

An implantable tissue guide was developed in order to deliver an aligned collagen gel seeded with Schwann cells to the site of a nerve repair in the rat. The outer element was made from a tube of silicone (Medical grade; length 10 mm, outer diameter 3.17 mm, inner diameter 1.98 mm; obtained from VWR). The silcone tube was perforated around each end using a 19G hypodermic needle to leave two rings of 8 holes of 0.5 mm-1 mm diameter. The perforations enabled the collagen to integrate with the tube at these end regions.

Collagen gels were created with Schwann cells as described above, but instead of pouring the gels into moulds, gel was squirted from a pipette into the perforated silicone tube. Sufficient gel was used to completely fill the lumen of the tube and to integrate with the ends by flowing out of the perforations. 2.5 ml of gel was used to fill 10 tubes, which were then left to set in a Petri dish for 5 min at 37° C. The filled tubes were then carefully separated from each other and any excess collagen trimmed away prior to overnight incubation in culture media containing DMEM+10% FCS supplemented with 50 µg/ml ascorbic acid.

During this incubation, the gel contracted within the tube and pulled away from the walls of the tube in the middle, whilst remaining tethered at its ends. This resulted in a thin strand of collagen containing aligned Schwann cells running down the centre of the tube, held in place at the ends of the tube Constructs were assessed for contraction of gel and integrity of tethering using an inverted stage phase contrast microscope. For example, staining the gel with haematoxylin and eosin showed the cells, and a phase contrast image of an unstained section from the same construct showed its position in the tube.

Implantation of Self-Aligned Collagen Device

Female Fisher rats (150-200 g, Harlan, n=27) were randomised into three equal experimental groups and deeply anaesthetised using Isoflourane administered by inhalation.

Using a dissecting microscope, the left sciatic nerve of each animal was exposed in mid-thigh and a 5 mm section of nerve excised. Devices containing self aligned collagen and Schwann cells were implanted into one group of animals, whilst the second group received empty silicone tubes of equal length. Conduits were held in place using four 10/0 epineurial sutures at each stump. The final experimental group was left with a 5 mm interstump gap (i.e. no device was implanted). Wounds were closed in layers and animals allowed to recover.

Three animals from each experimental group were sacrificed by $CO_2$ asphyxiation at 2, 4 and 8 weeks after surgery. Nerves were re-exposed and a 25 mm length of nerve incorporating the surgical site was excised under a dissecting microscope. Nerves and conduits or controls were then immersion fixed overnight in 4% paraformaldehyde. Tissue was then embedded in polyester wax and 7 µm sections of the implant site with nerve stumps (in longitudinal section) and of the distal stump 1 cm distal to the implant site (in transverse section) were cut. Sections were then double immunostained using mouse monoclonal anti-200 kD neurofilament to identify regenerating axons visualised with anti-mouse FITC (Sigma 1:100) and rabbit polyclonal anti-S100 to identify Schwann cells (DAKO, diluted 1:200) visualised with anti-rabbit TRITC (Sigma, diluted 1:100). Primary antibodies were incubated overnight at 40° C. and secondary antibodies were incubated at room temperature for one hour.

Quantification of Regeneration

Regeneration was quantified at both the implant site and also at 1 cm distal from the proximal end of the distal stump. To quantify regeneration across the nerve defect, three longitudinal sections separated by 100 µm were randomly chosen from each animal and immunostained as described previously. A digital image of the exact centre of the interstump region of each section was then captured using a Zeiss Axio-Cam HRm camera combined with Zeiss Axiovision software attached to a Olympus Provis fluorescence microscope. The area of the image immunostained with anti-neurofilament antibody was then calculated using Zeiss KS-300 image analysis software.

Regeneration was also quantified distal to the transection site by calculating the percentage of S-100 immunoreactive Schwann cell tubes containing neurofilament immunoreactive axons in transverse sections of nerve taken 1 cm distal from the proximal end of the distal stump. Statistical analyses of the results were performed using one-way ANOVA with Bonferoni's multiple comparison post-tests.

Results

Aligned Collagen Gels Orientated Neurones In vitro

Rectangular Schwann-cell seeded collagen gels were tethered at their ends for 18 hours then immunostained using an antibody against the Schwann cell marker S100. Confocal microscope projections revealed that the Schwann cells within the gels became aligned along the axis of tension formed by the tethering alignment (i.e. parallel to the long axis of the gel). The presence of the tethering bars at each end of rectangular collagen gels provides triangular regions that are stress-shielded (termed delta-zones) (Eastwood et al., 1998. Cell Motil Cytoskeleton 40:13-21). Schwann cell processes were observed to develop with random orientation in these delta zones. The delta zones therefore provided a useful control region in which the contracted cells within the gel are not aligned axially.

DRG neurones which were seeded onto this aligned substrate grew parallel to the axis of tension, (i.e. were orientated with the aligned Schwann cells), with the majority of axons showing a deviation of less than 10° (FIG. 1). Conversely, in the delta zones the DRG neurones grew in all directions.

Neuronal Growth is Improved by Tissue Guides In vivo

Figure 2:
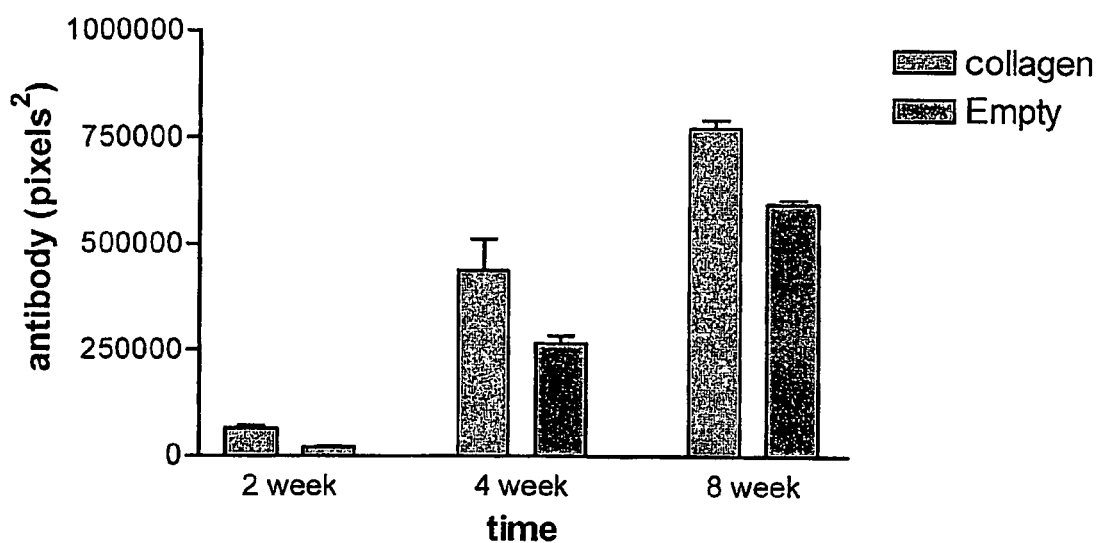
FIG. 2 shows immunofluorescent data which indicates the amount of neurofilament present in the distal stump of the repaired nerves in rats implanted with collagen-containing tissue guides compared to empty tubes.
Figure 3:
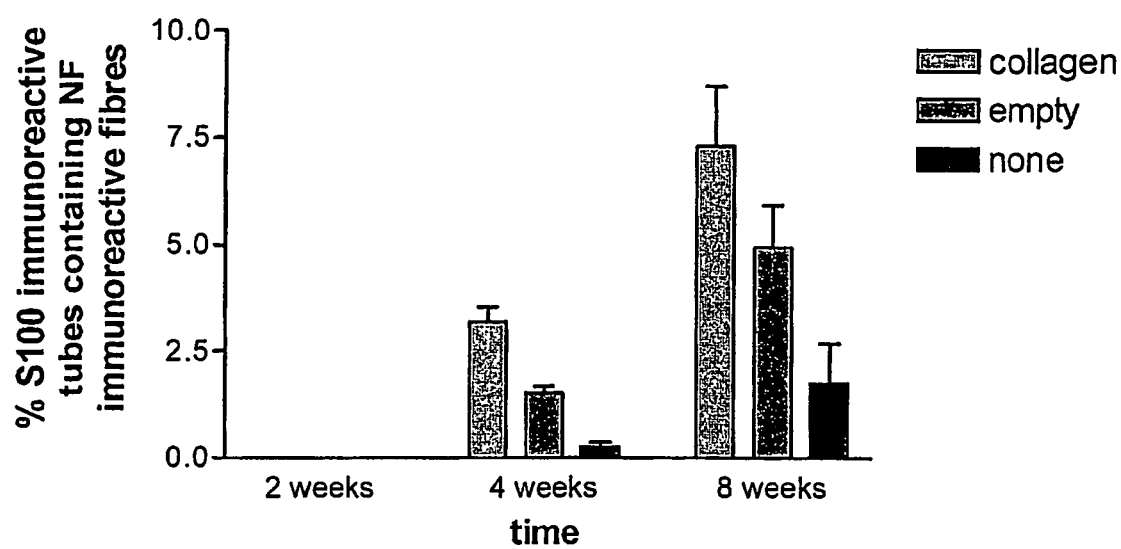
FIG. 3 shows immunofluorescent data which indicates the number of Schwann cell tubes containing regenerating axons in the rats implanted with collagen-containing tissue guides compared to empty tube or no repair controls after 2, 4, and 8 weeks.

An implantable tissue guide for nerve repair was developed using a silicone outer tube as described herein. Guides were implanted into a model of peripheral nerve injury in the rat. Neuronal regeneration was significantly greater after 4 and 8 weeks in rats that received the cellular collagen device compared to an empty silicone tube or no repair. FIG. 2 shows the quantity of neurofilament present in the distal stump of the repaired nerves as determined by quantification of immunofluorescent longitudinal section images. This gave an indication of the level of neuronal regeneration across the gap and showed that at each time point this was greater in the presence of contracted collagen compared to empty tube controls. A further assessment of regeneration comprised quantification of the number of S100 positive Schwann cell tubes which contained neurones positive for neurofilament in transverse sections 1 mm distal to the distal stump. Prior to transection, all Schwann cell tubes will have contained neurones and subsequent Wallerian degeneration will leave these tubes empty for occupation by regenerating axons. FIG. 3 shows that after 4 and 8 weeks, significantly more Schwann cell tubes contained regenerating axons in the rats that received collagen-containing devices compared to empty tube or no repair controls.

Tethering opposing ends of collagen gels that are seeded with contractile cells is shown herein to promote the formation of an aligned cellular construct. This substrate provides guidance cues that result in highly aligned neuronal growth from DRGs when compared to the randomly aligned delta zones. Implantation of aligned tissue guides containing cellular collagen matrices into sites of peripheral nerve injury is shown to increase nerve growth, both in terms of absolute neuronal tissue detected in the distal stump, and the number of innervated Bands of Büngner distal to the repair.

The invention claimed is:

1. A tubular tissue growth guide comprising:
   an inner core comprising a biopolymer matrix seeded with cells;
   an outer sheath surrounding said inner core;
   said inner core being tethered to said outer sheath only at opposing ends of said guide;
   said seeded cells providing mechanical tension in said core between the tethered opposing ends.

2. A tubular guide according to claim 1, wherein the mechanical tension in said core causes alignment of the cells.

3. A tubular guide according to claim 1, wherein the mechanical tension in said core causes alignment of the fibres of said biopolymer matrix.

4. A tubular guide according to claim 1, wherein the biopolymer matrix is a collagen matrix.

5. A tubular guide according to claim 1 adapted for use as an implant in the repair of damaged tissue.

6. A tubular guide according to claim 1, wherein said seeded cells comprise one or more of Schwann cells, neural fibroblasts, fibroblasts, tenocytes, astrocytes, osteoblasts, myoblasts, melanocytes, smooth muscle cells, secretory or gland vessel cells, epithelial cells and endothelial cells.

7. A tubular guide according to claim 1, wherein said outer sheath is biosorbable.

8. A tubular guide according to claim 1, wherein said outer sheath is non-porous.

9. A tubular guide according to claim 1, wherein said outer sheath is selected from the group consisting of silicone, phosphate glass, polylactone, polyglycone, polycapryolactone, hyaluronan or derivatives thereof, collagen, fibrin, fibronectin, cellulose, chitosan, and starch.

10. A tubular guide according to claim 1, wherein said outer sheath is shaped to cooperatively engage the inner core at the tethered ends to prevent co-axial movement of the core relative to said outer sheath.

11. A tubular guide according to claim 1, wherein said outer sheath is chemically fixed to the core at the tethered ends.

12. A guide according to claim 1 adapted for in vitro use as a bioreactor for the growth of tissue.

13. A tubular guide according to claim 5, wherein the outer sheath comprises one or more entry ports for entry of regenerating tissue.

14. A tubular guide according to claim 5 adapted for the regeneration of nerves.

15. A tubular guide according to claim 5, wherein the mechanical tension in the core imparts traction on regenerating tissue in the guide.

16. A tubular guide according to claim 6, wherein said cells comprise Schwann cells and fibroblasts.

17. A tubular guide according to claim 10, wherein said outer sheath comprises one or more openings which cooperatively engage the inner core at the opposing ends.

18. A tubular guide according to claim 14, wherein the outer sheath comprises an entry port for entry of regenerating nerve and an exit port for exit of a regenerating nerve.

19. A tubular guide according to claim 17, wherein said openings comprise a plurality of pores.

20. A tubular guide according to claim 17, wherein said openings comprise one or more holes in said outer sheath.

21. A tubular guide according to claim 18 comprising one or more fixings for fixing in place the entry point adjacent to the proximal end of a damaged nerve and the exit point at the distal end of a damaged nerve.

22. A method of making a guide for tissue growth comprising:
   providing an outer sheath;
   introducing cells to a liquid biopolymer matrix to produce a cell seeded matrix;
   introducing said cell seeded matrix to the interior of the outer sheath;
   causing or allowing said cell seeded matrix to set; and
   fixing said cell seeded matrix to said outer sheath to tether said cell seeded matrix to only the opposite ends of said outer sheath.

23. A method according to claim 22, wherein said outer sheath cooperatively engages said cell seeded matrix at the opposing ends of said outer sheath said tethering preventing co-axial movement of the core relative to said outer sheath.

24. A method of facilitating growth of tissues in a human or animal body comprising implanting a tubular tissue growth guide of claim 1 into a human or animal body in need of said facilitating.

25. A method according to claim 22, wherein the cells comprise fibroblasts and one or more cells of said tissue.

26. A method according to claim 22, wherein the tissue cells comprise fibroblasts and one or more stem cells or progenitor cells of cells of said tissue.

27. A method of claim 24, further comprising linking ends of said tissue growth guide to broken ends of a damaged tissue in the human or animal; and
   allowing said tissue to regenerate through said tubular tissue growth guide.

28. A method according to claim 27, wherein the damaged tissue is a nerve.

* * * * *